US009714409B2

(12) United States Patent
Rasanayagam et al.

(10) Patent No.: US 9,714,409 B2
(45) Date of Patent: Jul. 25, 2017

(54) USE OF ARGON AS A TISSUE FIXATION PRESERVATIVE

(71) Applicants: American Air Liquide, Inc., Fremont, CA (US); The United States of America as Represented by the Secretary, Dept. of Health and Human Svcs., National Institutes of Health, Washington, DC (US)

(72) Inventors: Vasuhi Rasanayagam, Newark, DE (US); Sagar D. Joshi, Newark, DE (US); Meenakshi Sundaram, Newark, DE (US); Stephen M. Hewitt, Rockville, MD (US); Joon-Yong Chung, Rockville, MD (US)

(73) Assignees: American Air Liquide, Inc., Fremont, CA (US); The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/422,062

(22) PCT Filed: Aug. 16, 2013

(86) PCT No.: PCT/US2013/055337
§ 371 (c)(1),
(2) Date: Feb. 17, 2015

(87) PCT Pub. No.: WO2014/028839
PCT Pub. Date: Feb. 20, 2014

(65) Prior Publication Data
US 2015/0216161 A1 Aug. 6, 2015

Related U.S. Application Data

(60) Provisional application No. 61/684,204, filed on Aug. 17, 2012.

(51) Int. Cl.
| | | |
|---|---|---|
| C12N 1/04 | (2006.01) | |
| B01J 19/00 | (2006.01) | |
| C12Q 1/68 | (2006.01) | |
| A01N 1/00 | (2006.01) | |

(52) U.S. Cl.
CPC ............... *C12N 1/04* (2013.01); *A01N 1/00* (2013.01); *C12Q 1/6806* (2013.01)

(58) Field of Classification Search
CPC .................................................... C12N 1/04
USPC ................................ 435/6.1, 260; 422/40
See application file for complete search history.

(56) References Cited

U.S. PATENT DOCUMENTS

2010/0196996 A1* 8/2010 Kilic .................. A01N 1/00
435/260

FOREIGN PATENT DOCUMENTS

WO WO 2010 088364 8/2010

OTHER PUBLICATIONS

"RNA integrity is paramount to accurate gene expression analysis," downloaded from http://www.agendia.com/pages/rna_integrity/42.php on Aug. 6, 2012, 2 pp.
Abramovitz, M. et al., "Optimization of RNA extraction from FFPE tissues for expression profiling in the DASL assay," BioTechniques, vol. 44, No. 3, 2008, 417-423.
Chung, J.-Y. et al., "Factors in tissue handling and processing that impact RNA obtained from formalin-fixed, paraffin-embedded tissue," Journal of Histochemistry & Cytochemistry 2008 56(11) 103-1042.
Fleige, S. et al., "RNA integrity and the effect on the real-time qRT-PCR performance," Molecular Aspects of Medicine 27 (2006) 126-139.
Groelz, D. et al., "Non-formalin fixative versus formalin-fixed tissue: a comparison of histology and RNA quality," Experimental and Molecular Pathology, vol. 94, issue 1, Feb. 2013, 188-194.
Hewitt, S.M. et al., "Tissue handling and specimen preparation in surgical pathology: issues concerning the recovery of nucleic acids from formalin-fixed, paraffin-embedded tissue," Review Article, Arch Pathol Lab Med, vol. 132, Dec. 2008, 1929-1935.
Okello, J.B.A. et al., "Comparison of methods in the recovery of nucleic acids from archival formalin-fixed paraffin-embedded autopsy tissues," Analytical Biochemistry 400 (2010) 110-117.
Srinivasan, M. et al., "Effect of fixatives and tissue processing on the content and integrity of nucleic acids," Review, American Journal of Pathology, vol. 161, No. 6, Dec. 2002, 1961-1971.
Van 'T Veer, L.J. et al., "Gene expression profiling predicts clinical outcome of breast cancer," Nature, vol. 415, Jan. 31, 2002, 530-536.
Von Ahlfen, S. et al., "Determinants of RNA quality from FFPE samples," PLoS ONE, Dec. 2007, Issue 12, e1261, 7 pp.
Xie, R. et al., "Factors influencing the degradation of archival formalin-fixed paraffin-embedded tissue sections," Journal of Histochemistry & Cytochemistry 2011 59(4) 356-365.
International Search Report and Written Opinion for PCT/US2013/055337, Oct. 24, 2013.
Fergenbaum, J.H., et al., Loss of antigenicity in stored sections of breast cancer tissue microarrays, Cancer Epidemiol Biomarkers Prev, 13(4), pp. 667-672, Apr. 2004.
Gray, R.G., et al., Validation study of a quantitative multigene reverse transcriptase-polymerase chain reaction assay for assessment of recurrence risk in patients with stage II colon cancer, Journal of Clinical Oncology, 29(35), pp. 4611-4619, Dec. 2011.

(Continued)

*Primary Examiner* — Jezia Riley
(74) *Attorney, Agent, or Firm* — Allen E. White

(57) ABSTRACT

The invention may be broadly defined as the addition of Argon to FFPE procedures as an RNA stabilizing agent. Argon is an inert gas from the Noble gas group with low saturation concentrations in water. It is therefore highly surprising that Argon would have any effect on RNA stability in the presence of Formalin, or any other chemical. This property of Argon appears to be specific in that other inert gases fail to show any RNA stabilizing effect.

17 Claims, 7 Drawing Sheets

(56) References Cited

OTHER PUBLICATIONS

Olert, J., et al., HOPE Fixation: A novel fixing method and paraffin embedding technique for human soft tissues, Pathol Res Pract 197, pp. 823-826, 2001.
Sutour, C., et al., Determination of the argon concentration in ambient dry air for the calculation of air density, Metrologia 44, pp. 448-452, 2007.

\* cited by examiner

USE OF ARGON AS A TISSUE FIXATION PRESERVATIVE

CROSS REFERENCE TO RELATED APPLICATIONS

This application is a 371 of International Application No. PCT/US2013/055337 filed Aug. 16, 2013 which claims the benefit of U.S. provisional application No. 61/684,204, filed Aug. 17, 2012, the entire contents of each being incorporated herein by reference.

This invention was created in the performance of a Cooperative Research and Development Agreement (NCI CRADA 2544) with the National Institutes of Health, an Agency of the Department of Health and Human Services. The Government of the United States has certain rights in this invention.

BACKGROUND

Technical Field

The disclosure relates to the fixation of tissue samples for subsequent studies such as histopathology analysis.

Background Art

Biological tissue specimens are collected in many different circumstances and for a variety of scientific and medical purposes. One category of tissue specimens is collected for medical research and diagnostics of both humans and animals. An example subcategory is human tumor samples for oncology related studies.

Historically, tissue samples have been fixed and stained with a variety of chemicals to produce colorimetric indications of various features in the tissue. In medical diagnostics, this is generally referred to as histopathology. The basic process involves staining with dyes to produce contrasting colors for cellular elements. An example is Hematoxylin which is used to stain cell nuclei blue, plus eosin to stain cytoplasm and the extracellular matrix pink (called an H&E stain). Layered onto these background stains are histochemical reaction products e.g. to detect excess iron or copper and immunohistochemical staining procedures used to ascertain the presence of specific biomolecules e.g. proteins, specific nucleic acid structures, etc.

To the foregoing, medical science is adding a new dimension to histopathology to support what is broadly termed "personalized medicine" or "molecular medicine." These broad terms encompass current histopathology techniques, in particular immunohistochemistry. However a key component of the new histopathology paradigm is the analysis of specific biomolecules in cells, specifically deoxyribonucleic acids (DNA) and ribonucleic acids (RNA) and proteins and/or post-translationally modified proteins involved in cellular processes. DNA is most often associated with characteristic genetic changes in certain cancers and inherited genetic diseases. The presence and condition of RNA is a downstream indicator showing for example how active genes are in cells. Much of personalized medicine focuses on gene activity as reflected by RNA. The presence, absence, or quantitative amounts of RNA, and the relative amounts of specific RNAs to each other, all serve to form an "expression profile" or "gene expression signature." The measurement of proteins involved in intra-cellular signaling, and specifically post-translational modifications to proteins, such as their phosphorylation status can provide critical information on the behavior of specific cell populations.

The use of gene expression profiling in personalized medicine is no longer a technology of the distant future. An example is the AGENDIA® MAMMAPRINT®, an RNA expression profile diagnostic approved by the FDA for determining the risk of long term breast cancer metastasis. See generally, van't Veer L J Dai H, van de Vijver M J, et al. (2002). "Gene expression profiling predicts clinical outcome of breast cancer". Nature 415 (6871): 530-6. doi: 10.1038/415530a; U.S. FDA 510(k) approval number K062694. As discussed for the AGENDIA® MAMMAPRINT® in its product literature, RNA integrity is critical for the effective use of expression profiling technology. The MAMMAPRINT® U.S. FDA label requires therefore a minimum level of RNA integrity.

Tissue specimens are archived for standard histopathology study using formalin-fixation with paraffin embedding (FFPE). FFPE damages RNA to a degree that archived tissue normally cannot be used for expression profile tests such as MAMMAPRINT® without great difficulty. There have however been some tests developed where the expression profile can be determined despite the poor quality of FFPE extracted RNA. See, e.g. Gray, Richard G., et al. "Validation study of a quantitative multigene reverse transcriptase-polymerase chain reaction assay for assessment of recurrence risk in patients with stage II colon cancer." *Journal of Clinical Oncology* 29.35 (2011): 4611-4619 (commercially sold as the Oncotype DX® colon cancer assay). These current FFPE extracted RNA assays rely on small RNA fragments, detected by hybridization or very short PCR amplicons, both of which limit the genes that can be evaluated. Even existing FFPE extracted RNA based tests could be improved by providing better RNA from FFPE tissue samples. Currently, RNA must be maintained by an alternative treatment of the tissue than FFPE such as the RNA extraction systems sold under the RNAlater® and RNAretain® trademarks and described in U.S. Pat. No. 6,204,375 and subsequent patents. These alternative RNA preservation techniques are not retroactively applicable and have not been successfully adopted for clinical applications.

A problem presented by the emergence of molecular diagnostics of RNA in tissue samples is the integration of such RNA testing with standard archival fixation of tissues samples. Any integrated change should not affect current histopathology procedures such as H&E staining.

Efforts to solve this integration problem have primarily focused of replacing FFPE with more RNA friendly fixation chemistries that are simultaneously compatible with current histopathology stains. One example is the HOPE tissue fixation technique. Jürgen Olert, et al., "HOPE-fixation: A novel fixing method and paraffin embedding technique for human soft tissues" (2001) Pathol Res Pract 197:823-826. Other RNA preserving tissue fixation chemistries have been offered commercially (e.g. the PAXgene® Tissue System).

HOPE tissue fixation and other techniques have not replaced FFPE in standard tissue sample preservation procedures, despite being available for over a decade. The problem to be solved then may be defined as providing a way to modify current FFPE procedures to enhance RNA stability with as little effect as possible on the FFPE process and the histopathology staining of the resulting fixed tissues. Ideally, the FFPE procedure modifications may be easily integrated into existing procedures and equipment and at a cost that does not de facto prohibit implementation.

RNA degradation in FFPE procedures has been studied thoroughly and described in the art recognized authoritative papers on the subject. Stephen M. Hewitt, Fraser A. Lewis, Yanxiang Cao, Richard C. Conrad, Maureen Cronin, Kathleen D. Danenberg, Thomas J. Goralski, John P. Langmore, Rajiv G. Raja, P. Mickey Williams, John F. Palma, and Janet A. Warrington, "Tissue Handling and Specimen Preparation in Surgical Pathology: Issues Concerning the Recovery of Nucleic Acids From Formalin-Fixed, Paraffin-Embedded Tissue", Archives of Pathology & Laboratory Medicine 2008 132:12, 1929-1935; Joon-Yong Chung, Till Braunschweig, Reginald Williams, Natalie Guerrero, Karl M. Hoffmann, Mijung Kwon, Young K. Song, Steven K. Libutti, Stephen M. Hewitt, "Factors in Tissue Handling and Processing That Impact RNA Obtained From Formalin-fixed, Paraffin-embedded Tissue", J Histochem Cytochem. 2008 November; 56(11): 1033-1042. doi: 10.1369/jhc.2008.951863.

While much is unknown regarding the factors at play in RNA degradation, the RNA degradation profile during FFPE is generally known as summarized in FIG. 1. As can be seen, once the tissue specimen is fixed and embedded, the RNA degrades only very slowly over time. The bulk of RNA degradation occurs during FFPE processing and fixation. The mechanisms of RNA degradation pre- and post-processing (i.e. post paraffin embedding) are distinct. For example, the chemical modifications of RNA by Formalin during fixation are known to involve RNA fragmentation and chemical crosslinking to proteins and other biomolecules in the tissues.

FFPE processes are diverse in various aspects. The foregoing papers have surveyed and identified some optimal FFPE conditions and best practices for RNA stability such as the use of phosphate buffered Formalin over other buffer systems. However, these optimized practices alone will often not be sufficient to produce fixed tissues that are viable RNA sources for gene expression profile studies. The following disclosure therefore provides a solution to the foregoing problem(s) of poor RNA stability during FFPE procedures.

DISCLOSURE OF INVENTION

The invention may be broadly defined as the addition of Argon to FFPE procedures as an RNA stabilizing agent. Argon is an inert gas from the Noble gas group with low saturation concentrations in water. It is therefore highly surprising that Argon would have any effect on RNA stability in the presence of Formalin, or any other chemical. This property of Argon appears to be specific in that other inert gases fail to show any RNA stabilizing effect. The failure of other inert gases (e.g. Nitrogen) to stabilize RNA in FFPE also indicates that the Argon is not functioning by displacement of atmospheric gases. To the extent the effects of Argon on RNA stability in tissue can be reasonably inferred, one would predict that Argon would enhance RNAase activity and thus exacerbate RNA degradation rates in tissue samples. See U.S. Pat. No. 5,462,861, Col. 10, lines 40-45. The mechanism of action by Argon in this context is thus unknown and there is no clear basis for a reasonable hypothesis. Despite this, Argon is empirically shown as capable of improving RNA integrity by an astonishing 40% over control FFPE procedures.

The general process for Formalin fixation paraffin embedding (FFPE) is shown in FIG. 2 (adapted from figure one of Joon-Yong Chung, et al., "Factors in Tissue Handling and Processing That Impact RNA Obtained From Formalin-fixed, Paraffin-embedded Tissue", J Histochem Cytochem. 2008 November; 56(11): 1033-1042.). Argon may be added to any and all FFPE liquid reagents and also provided as a controlled gas atmosphere in contact with the liquid reagents.

Argon Addition to Liquid Reagents

Argon addition may be achieved through any available means such as gas sparging or bubbling through a liquid reagent and/or storage of a liquid reagent in contact with an Argon atmosphere. Such Argon conditioning may be for a sufficient period of time to a) saturate the liquid reagent and/or b) strip out any air gases dissolved in the liquid reagent.

Controlled Atmosphere with Argon

Containers holding a tissue sample may be flushed with e.g. industrial grade, preferably medical grade, Argon gas and then quickly sealed to provide an Argon enriched atmosphere in contact with a liquid reagent. A container may alternatively be adapted to allow purging of the atmosphere within the container to produce a substantially pure Argon atmosphere (e.g. 90%-99% Argon such as 95% Argon/balance Nitrogen). The container may be further adapted to receive and maintain the substantially pure Argon atmosphere at higher than atmospheric pressure (such as 1.01-2 standard atmospheres pressure).

"Argon", "Argon gas", "adding/added Argon", "Argon enriched" and similar terms are defined to mean an Argon gas level greater than that found in atmospheric air, which is approximately: $[Ar]>0.9330\times10^{-2}$ mol mol$^{-1}\pm0.0032\times10^{-2}$ mol mol$^{-1}$. *Determination of the argon concentration in ambient dry air for the calculation of air density*, C Sutour et al., 2007 *Metrologia* 44 448). In certain embodiments "Argon", "Argon gas", "adding/added Argon", "Argon enriched" and similar terms are more specifically defined to mean only an Argon gas level greater than that found in atmospheric air while all other atmospheric air gases (e.g. Oxygen, Nitrogen, Carbon Dioxide, Methane, Carbon Monoxide, and other Nobel gases) are at or below atmospheric air levels. In other embodiments, "Argon", "Argon gas", "adding/added Argon", "Argon enriched" and similar terms are more specifically defined to mean industrial grade Argon or a blend of and industrial grade or a higher purity Argon gas and industrial grade (e.g. 95%) or medical grade USP Nitrogen. Specific Argon/Nitrogen blend examples are 80%/20%, 75%/25%, 70%/30% or 50%/50% blends.

"Argon enriched" as applied to a liquid is defined as having a dissolved Argon level higher than that achieved by exposure of the same liquid to the Argon in atmospheric air at equilibrium at 25 degrees C. In certain embodiments, "Argon enriched" as applied to a liquid is more specifically defined as having a dissolved Argon level higher than that achieved by exposure of the same liquid to the Argon in atmospheric air at equilibrium at 25 degrees C.; while all other dissolved atmospheric gases remain at or below the level achieved by exposure of the same liquid atmospheric air at equilibrium at 25 degrees C.

"Industrial grade Argon" generally means ≥95% Argon such as ≥99.5% Argon with the balance being residual gases from cryogenic distillation. Some preferred forms of industrial grade Argon are:

| | | | | |
|---|---|---|---|---|
| Moisture | <0.5 ppm | <3 ppm | <5 ppm | <3 ppm |
| Oxygen | <0.5 ppm | <2 ppm | <5 ppm | <2 ppm |
| Total Hydrocarbons | <0.1 ppm | <0.5 ppm | <2 ppm | <0.5 ppm |
| Carbon Dioxide | <0.5 ppm | <1 ppm* | | <1 ppm* |
| Carbon Monoxide | <0.1 ppm | <0.5 ppm* | | <0.5 ppm* |
| Nitrogen | <5 ppm | <5 ppm* | | |
| Hydrogen | <0.1 ppm | | | |
| Purity | >99.9995% | >99.999% | >99.995% | >99.999% |

Any reference to Argon herein is expressly defined to include the subgenus of industrial grade Argon and any of the above species of industrial grade Argon.

"Argon saturation" as applied to a liquid is defined as having a maximum amount of dissolved Argon. For example, at 1 bar pressure and at 20 degrees C., distilled deionized water has an Argon saturation amount of 62 mg/L. Generally, Argon saturated liquids referenced herein will have at least that of saturated DDI water i.e. at least 62 mg Ar/L liquid or an Argon concentration of 0.015 M at 20 degrees C. and at 1 bar pressure.

"Tissue fixation reagent" is a reagent that preserves a sample of biological material (tissue or cells) as close to its natural state as possible in the process of preparing tissue for examination. The ideal fixation agent generally should 1) Not shrink or swell tissue; 2) Not distort or dissolve tissue parts 3) Render enzymes inactive 4) Kill bacteria and mold; and 5) Modify tissue constituents so that they retain their form for further processing. No current tissue fixation reagent can completely meet these idealized criteria but they are nonetheless sufficiently close to the ideal to be useable for histopathology purposes. See Theory and Practice Histological Techniques, John Boeroff and Alan Stevens, Pat, 1980. Neutral Buffered Formalin (10%) solution, which contains 3-4% formaldehyde, 1-1.5% methanol and less than 1% phosphate buffer, is a well known fixative that is sufficient for all the foregoing requirements to be widely used (e.g. NBF modifies some tissue constituents but in a known and reproducible way). Other fixation reagents include 70% ethanol and those that are based on gluteraldehyde or acetone as the active fixation agents (e.g. commercial HOPE fixation with HOPE I & II solutions).

"Tissue processing reagent" is a reagent used after fixation in several steps of tissue processing. The processing steps generally are dehydration, clearing, and impregnation. Dehydration is aimed to remove water from the tissue. This is accomplished generally by soaking the fixed tissues in graded alcohol solutions (70%, 90%, 95% & 100% ethanol and/or isopropanol solutions). The clearing step is to remove the dehydration agent and it usually done by soaking the tissue in a xylene solution, isopropanol or commercially available xylene substitutes. Impregnation is the process of saturation of the tissue with a medium which prevents the tissue structure disruption. This is normally done with paraffin. See Histopathological methods and color atlas of special stains and tissue artifacts, by LEE.G Luna, Chap. 2.

"Tissue embedding reagent" is used to set the tissue specimen in a firm medium to keep the tissue intact during microtome sectioning. Normally paraffin is used for this purpose.

MODE(S) FOR CARRYING OUT THE INVENTION

Figure 1:
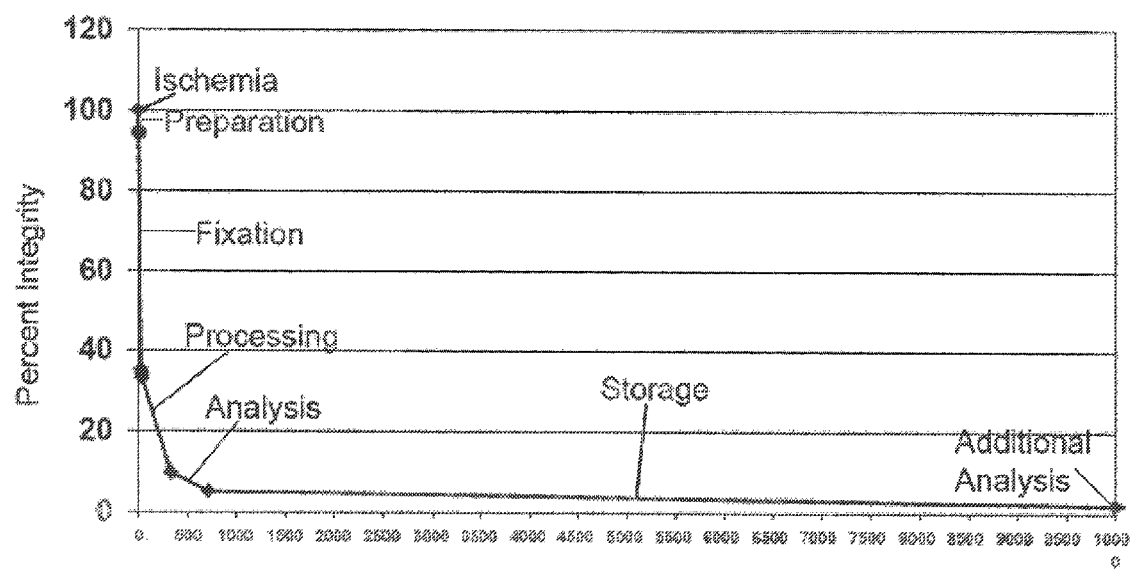
FIG. 1 shows the general apportionment of RNA degradation during and after FFPE procedures.
Figure 2:
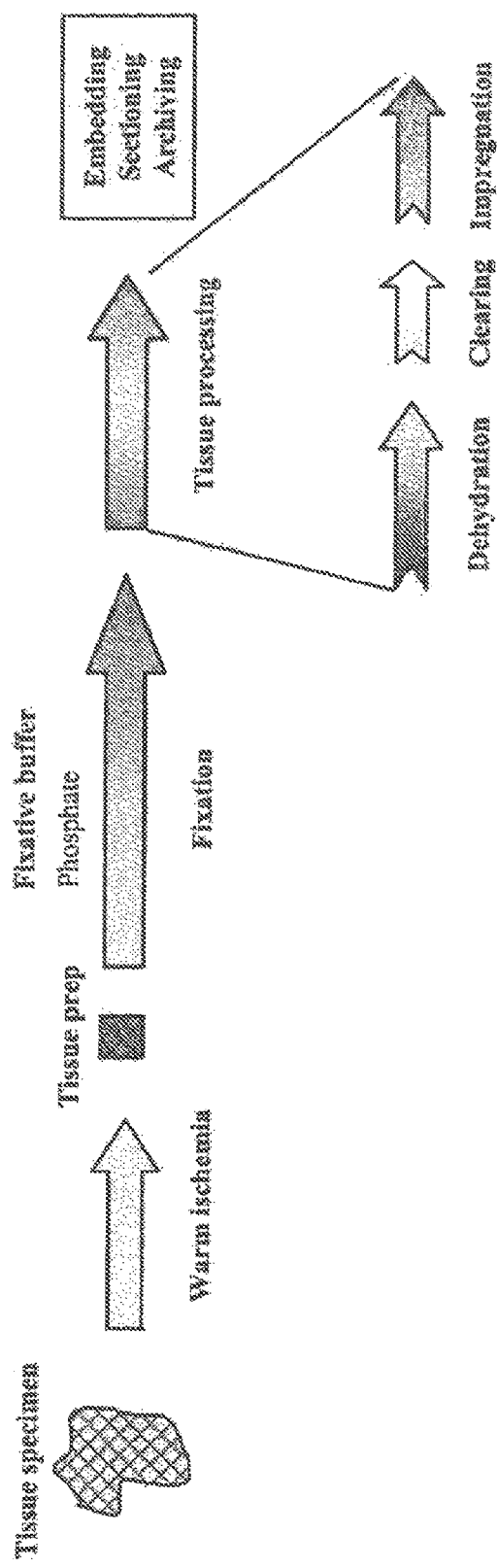
FIG. 2 shows the general process for Formalin fixation paraffin embedding (FFPE).

RNA is extracted from paraffin emended tissues using established procedures. (Okello J B., et al., 2010; Abramovitz M, et al, 2008).

RNA integrity is characterized by quantitative reverse transcriptase polymerase chain reaction (qRT-PCR) using fluorescently labeled nucleotides (Fleige S and Pfaffl M W, 2006). The comparative results are expressed as the number of PCR amplification cycles required to produce a discernible fluorescent amplification product signal. (Abramovitz M, et al, 2008; von Ahlfen S., et al, 2007). Comparisons are in terms of $ct_{experimental} - ct_{control} = \Delta ct$. A negative Δct thus represents an improvement in RNA quality. Due to the nature of PCR, the Δct values form a logarithmic scale axis when charted.

The qRT-PCR targets were the mRNAs for highly expressed liver "housekeeping" genes:

TABLE 1

Housekeeping Genes for ct Analysis

| Gene | Name | Species | Company | Catalog# | Amplicon length | Details |
|---|---|---|---|---|---|---|
| GUSB | glucuronidase, beta | Mouse | Invitrogen | Mm00446956_m1 | 88 | The assay probe spans an exon junction. |
| HPRT | hypoxanthine guanine phosphoribosyl transferase | Mouse | Invitrogen | Mm01545399_m1 | 81 | The assay probe spans an exon junction. |
| B2M | beta-2 microglobulin | Mouse | Invitrogen | Mm00437762_m1 | 77 | The assay probe spans an exon junction. |

The short amplicons produced by qRT-PCR from these highly expressed liver genes were selected to ensure measurable amplification products from the control FFPE samples.

Mice (C57BL/6J strain) were purchased from Jackson Laboratories. Livers were harvested by a third party, and shipped on dry ice.

Experiments 1-12: qRT-PCR Evaluation

Twelve independent experiments using experimental and matched control FFPE samples were performed. All fixation and processing liquid reagents were conditioned by Argon gas bubbling or blanketing as follows:

Argon was bubbled through a liquid fixative medium at ~2 scfh for about 15 min to remove other dissolved gas and saturate the solution with argon. Tissue specimens were added to this saturated liquid fixative medium with minimal exchange of atmospheric air. Low flow (~1 scfh) argon was sparged in the headspace to remove any air infiltration and to create a positive pressure in the head space in a container holding the liquid fixative medium and the specimen.

All the processing fluids are pre-conditioned with Ar (1.5 scfh) and the headspace of the containers are blanketed (1.5 scfh) with argon during presence of tissue.

The atmosphere in contact with all fixation and processing liquid reagents was maintained at high Argon concentration by flushing the headspace of containers and then rapidly sealing the container with the Argon atmosphere inside.

The FFPE procedure used is as follows:

| Chemical | Step | Quantity | Time | Temperature |
| --- | --- | --- | --- | --- |
| Formalin - Fixation | Fixation | 200 ml | 24 hrs | 22 deg C. |
| Formalin | Processing | 600 ml | 30 min | 22 deg C. |
| 70% Ethanol | Processing | 600 ml | 30 min | 22 deg C. |
| 95% Ethanol | Processing | 600 ml | 30 min | 22 deg C. |
| 95% Ethanol | Processing | 600 ml | 30 min | 22 deg C. |
| 100% Ethanol | Processing | 600 ml | 30 min | 22 deg C. |
| 100% Ethanol | Processing | 600 ml | 30 min | 22 deg C. |
| 100% Ethanol | Processing | 600 ml | 30 min | 22 deg C. |
| Xylene | Processing | 600 ml | 30 min | 22 deg C. |
| Xylene | Processing | 600 ml | 30 min | 22 deg C. |
| Wax | Impregnating | 1.1 lb | 30 min | 60 deg C. |
| Wax | Impregnating | 1.1 lb | 30 min | 60 deg C. |

Figure 3:
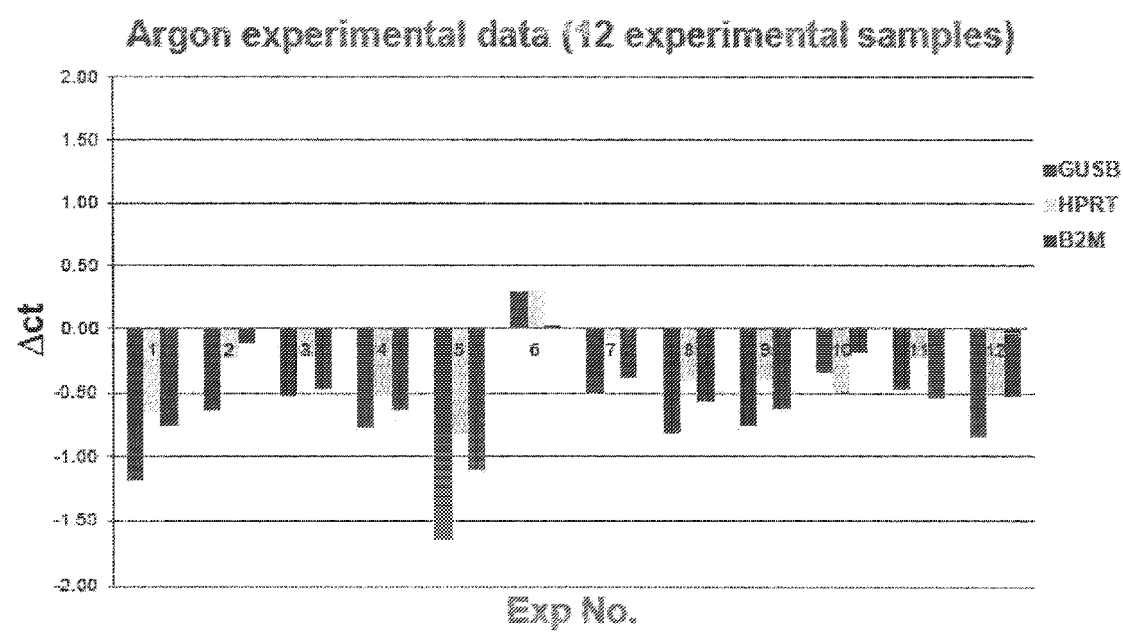
FIG. 3 shows the improvement in Δct values due to Argon conditioning of the fixation and processing liquid reagents plus an Argon atmosphere during all incubations.

The $\Delta$ct results are shown in FIG. 3. Argon reproducibly and significantly improves RNA integrity and stability in FFPE processed tissue specimens as assessed by qRT-PCR. The average $\Delta$ct is approximately −0.5 which corresponds to approximately 40% improvement in RNA quantity in the Argon treated FFPE samples relative to the control FFPE samples.

Figure 4:
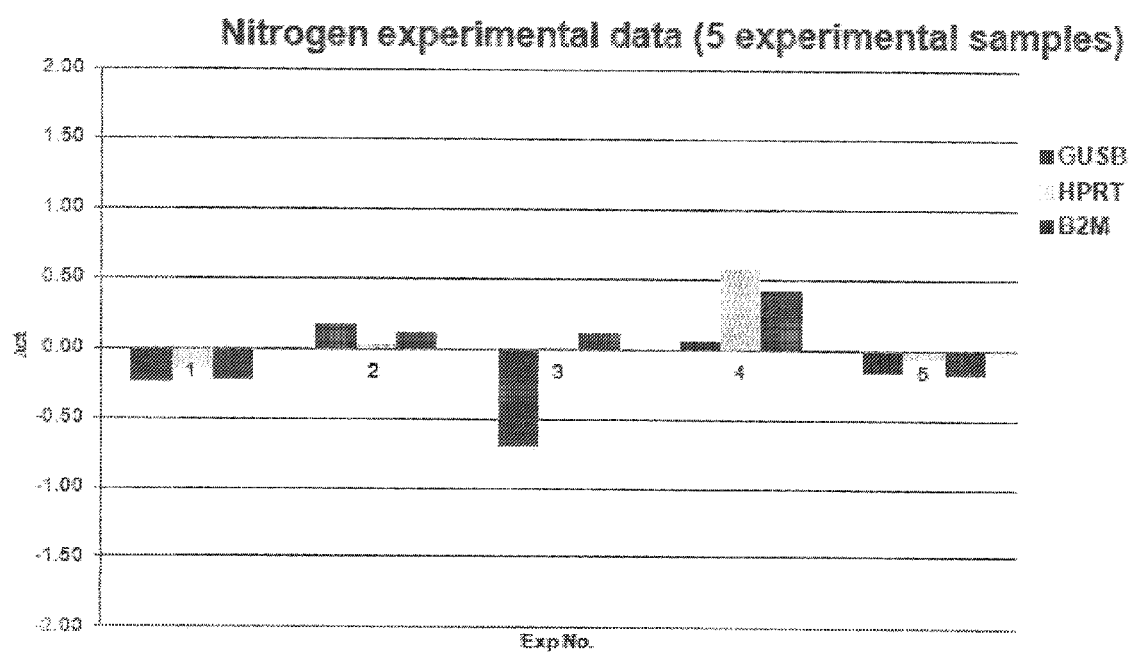
FIG. 4 shows the Δct values due to Nitrogen conditioning of the fixation and processing liquid reagents plus an Argon atmosphere during all incubations.

For comparison, the same procedures were followed but substituting Nitrogen gas for Argon gas. The results are shown in FIG. 4. Nitrogen has, on average, no effect on RNA stability.

As an alternative positive control, standard FFPE tissues were compared to RNA extracted directly from frozen livers i.e. without any fixation of processing. The Oct in these experiments averaged at approximately −1.5 to −2.0. Because the scale is logarithmic, the Argon results of −0.5 represent a small improvement over the maximum possible result or −2.0. Nonetheless, Argon sufficiently improves RNA quantities in FFPE tissues to allow for much more effective use of such Ar-FFPE derived RNA for expression profile analysis and other RNA based studies.

Examples: Protein Integrity

Figure 5:
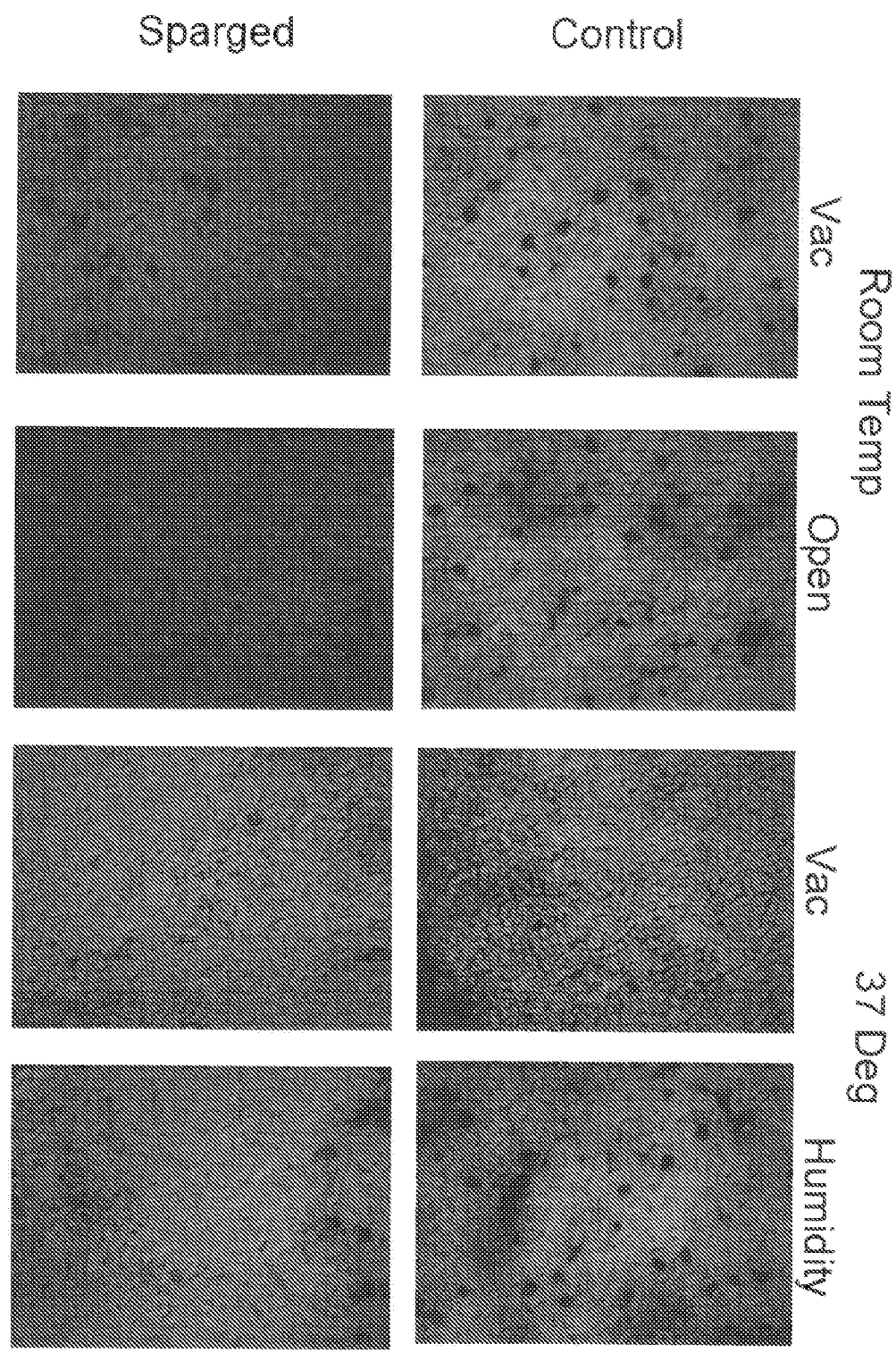
FIG. 5 are photomicrographs of eosin fluorescence of mouse kidneys slices comparing specimens fixed and processed in with air vs. sparged with nitrogen. Brighter=increased eosin fluorescence=increased N-termini=protein degradation; Darker=decreased eosin fluorescence=fewer N-termini=lesser or no protein degradation.

Ideally, the treatment of Argon enriched tissue fixation, processing and/or embedding reagents should not result in tissue samples with reduced immunohistochemical staining. To evaluate the impact of the above Argon enriched reagents, protein N-termini were assayed in representative tissue samples (shown in FIG. 5). FIG. 5 are photomicrographs of eosin fluorescence of mouse kidneys slices comparing specimens fixed and processed in with standard reagents ("air") or reagents sparged with nitrogen. Eosin fluorescence is quantitatively related to the number of N-termini of polypeptides. In the instance that the proteins are degrading, by hydrolysis, resulting in breaking of the peptide-backbone, there is a net increase in N-termini, and increased fluorescence. The Nitrogen sparged specimens demonstrate less degradation compared to the control specimens, when evaluated after storage at room temperature. The conditions of storage at 37 degrees are sufficiently harsh that the gains observed by sparging are lost. Similar results are observed with Argon.

These results indicate that reagents conditioned with Argon (or Nitrogen) improve protein integrity and will therefore produce superior immunohistochemical staining results. The result with Nitrogen is also informative in that Nitrogen does not improve qRT-PCR results. This highlights the distinction between preserving proteins and preserving RNA. These two distinct biomolecules are not predictably stabilized by the same conditioning gases. This also demonstrates that Argon does more than merely strip the other dissolved atmospheric gases from the treated reagents to yield RNA stability improvements.

Examples: Histopathology

Figure 6:
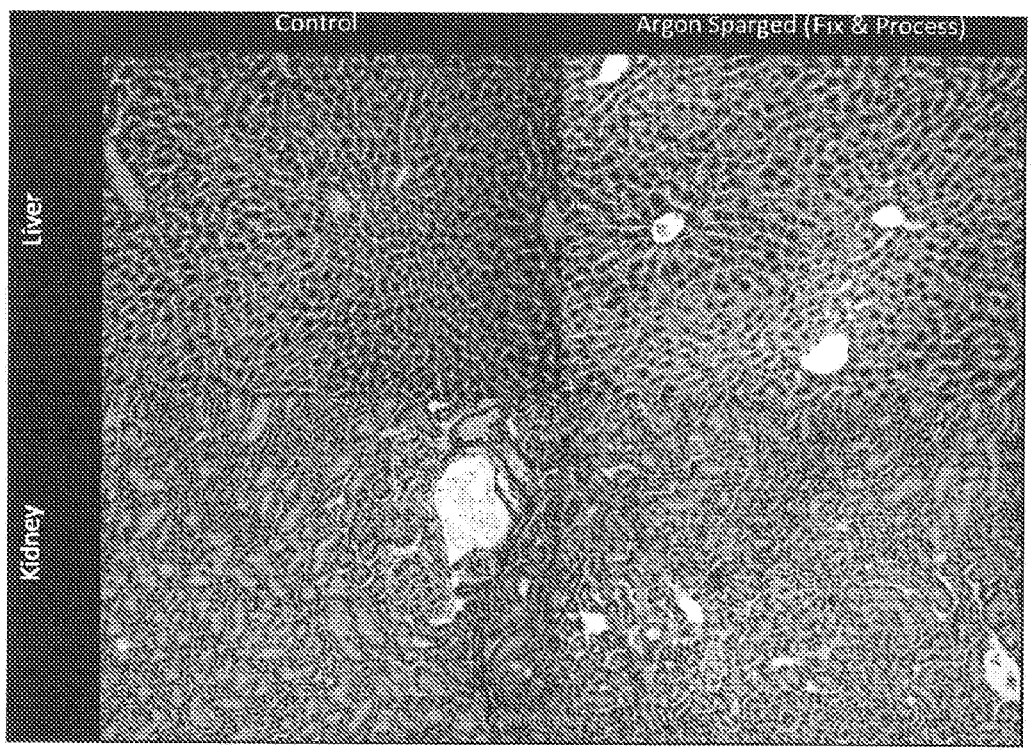
FIGS. 6-8 demonstrate comparisons of liver and kidney stained with H&E, with processing with either 10% neutral buffered formalin or 70% ethanol. While there are differences due to differences in Ethanol verses NBF, histomorphology is not impacted by the treatment of the fixatives or reagents with Nitrogen or Argon.
Figure 7:
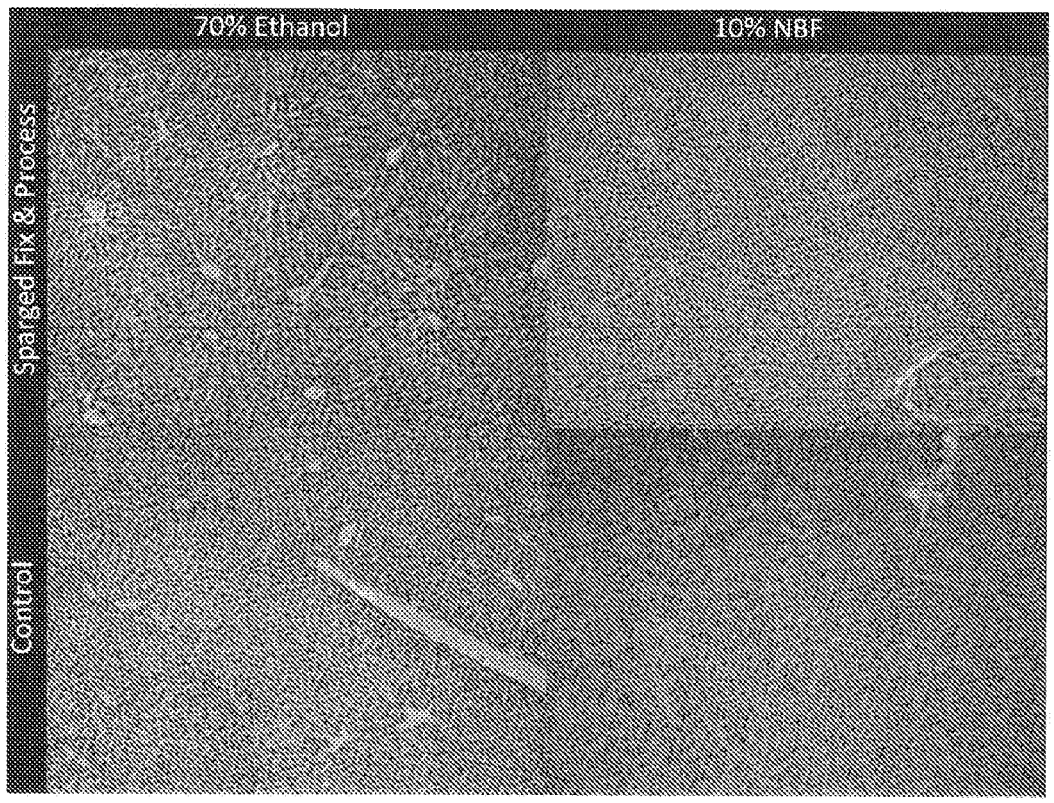
Figure 8:
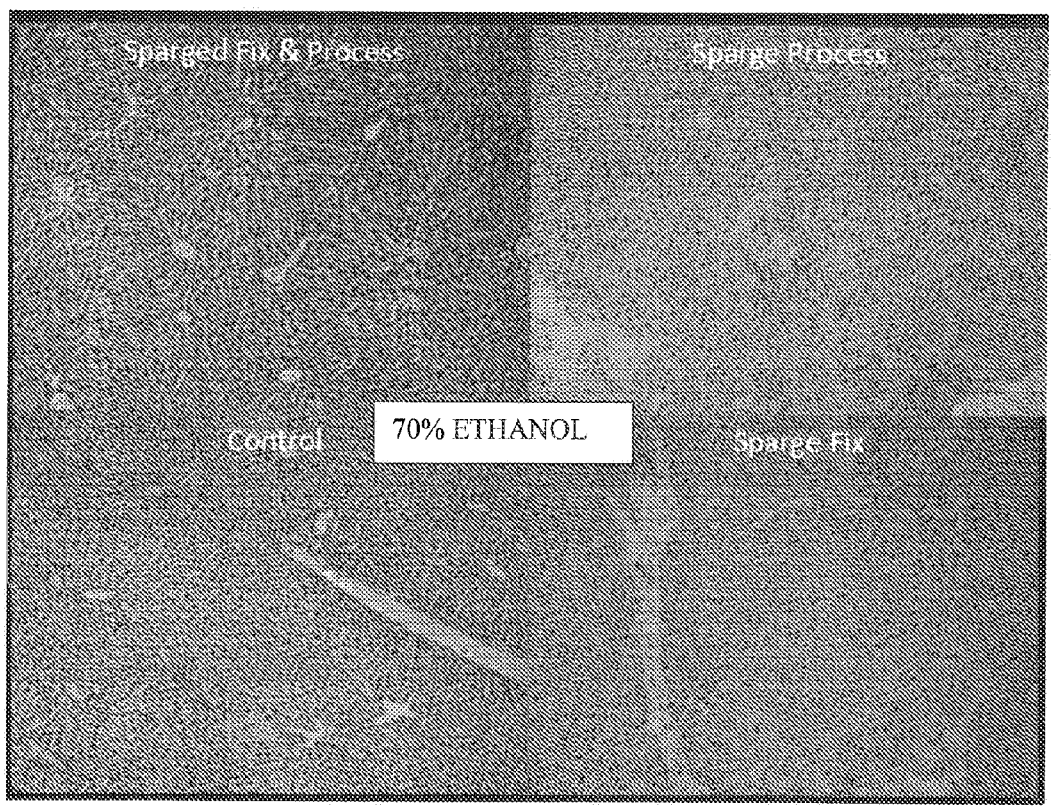

Hematoxylin and eosin stain (H&E stain or HE stain) is one of the most prevalent staining techniques applied to tissues for histopathology analysis. Histopathology evaluations of representative H&E stained tissue samples demonstrated that the use of Argon had no effect on this standard staining technique regardless of whether 10% neutral buffered formalin and 70% ethanol is used (FIGS. 6-8).

INDUSTRIAL APPLICABILITY

The present invention is at least industrially applicable to the fixation of biological tissue specimens for study of the histopathology and RNA contents.

REFERENCES

Factors influencing the degradation of archival formalin-fixed paraffin-embedded tissue sections., Xie R, Chung J Y, Ylaya K, Williams R L, Guerrero N, Nakatsuka N, Badie C, Hewitt S M., J Histochem Cytochem. 2011 Apr;59(4):356-65.

Srinivasan M, Sedmak D, Jewell S. 2002. Effect of fixatives and tissue processing on the content and integrity of nucleic acids. Am J Pathol. 161:1961-1971.

von Ahlfen S, Missel A, Bendrat K, Schlumpberger M (2007) Determinants of RNA Quality from FFPE Samples. PLoS ONE 2(12): e1261.

Optimization of RNA extraction from FFPE tissues for expression profiling in the DASL assay., Abramovitz M, Ordanic-Kodani M, Wang Y, Li Z, Catzavelos C, Bouzyk M, Sledge G W Jr, Moreno C S, Leyland-Jones B., Biotechniques. 2008 Mar;44(3):417-23.

Comparison of methods in the recovery of nucleic acids from archival formalin-fixed paraffin-embedded autopsy tissues. Okello J B, Zurek J, Devault A M, Kuch M, Okwi A L, Sewankambo N K, Bimenya G S, Poinar D, Poinar H N. Anal Biochem. 2010 May 1;400(1):110-7.

RNA integrity and the effect on the real-time qRT-PCR performance., Fleige S, Pfaffl M W., Mol Aspects Med. 2006 Apr-Jun;27(2-3):126-39.

Chung J Y, Braunschweig T, Williams R, Guerrero N, Hoffmann K M, Kwon M, Song Y K, Libutti S K, Hewitt S M. Factors in Tissue Handling and Processing That Impact RNA Obtained From Formalin-fixed, Paraffin-embedded Tissue. *J. Histochem. Cytochem.*56: 1033-42 2008. (Basis of experimental designs)

Hewitt S M, Lewis F A, Cao Y, Conrad R C, Cronin M, Danenberg K D, Goralski T J, Langmore J P, Raja R G, Williams P M, Palma J F, Warrington J A. Tissue handling and specimen preparation in surgical pathology: issues concerning the recovery of nucleic acids from formalin-fixed, paraffin-embedded tissue. *Arch. Pathol. Lab. Med.* 132: 1929-35, 2008. (Review article that summarizes field, need and prior literature)

Fergenbaum J H, Garcia-Closas M, Hewitt S M, Lisowska J, Sakoda L C, Sherman M E. Loss of antigenicity in stored sections of breast cancer tissue microarrays. *Cancer Epidemiol Biomarkers Prev.* 13: 667-72, 2004. (Initial data from NCI in this research space).

All references identified herein are each hereby incorporated by reference into this application in their entireties, as well as for the specific information for which each is cited.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step. The singular forms "a", "an" and "the" include plural referents, unless the context clearly dictates otherwise. "Comprising" in a claim is an open transitional term which means the subsequently identified claim elements are a nonexclusive listing i.e. anything else may be additionally included and remain within the scope of "comprising."

"Comprising" is defined herein as necessarily encompassing the more limited transitional terms "consisting essentially of" and "consisting of"; "comprising" may therefore be replaced by "consisting essentially of" or "consisting of" and remain within the expressly defined scope of "comprising". Optional or optionally means that the subsequently described event or circumstances may or may not occur. The description includes instances where the event or circumstance occurs and instances where it does not occur. Ranges may be expressed herein as from about one particular value, and/or to about another particular value. When such a range is expressed, it is to be understood that another embodiment is from the one particular value and/or to the other particular value, along with all combinations within said range.

The invention claimed is:

1. A method of stabilizing ribonucleic acid in biological tissue specimens comprising the steps of contacting a biological tissue specimen with an Argon enriched tissue fixation reagent, an Argon enriched tissue processing reagent or an Argon enriched tissue embedding reagent, and thereby stabilizing the ribonucleic acid in the biological tissue specimen against degradation as a result of said contacting.

2. The method of claim 1, further comprising the step of adding Argon to at least one of a tissue fixation reagent, a tissue processing reagent or a tissue embedding reagent prior to the contacting step.

3. The method of claim 2, further comprising a step of forming and maintaining an Argon enriched atmosphere in contact with one or more of the tissue fixation, processing and embedding reagents
    a) before contacting the biological tissue specimen with the tissue fixation, processing or embedding reagent,
    b) during an incubation of the biological tissue specimen with the tissue fixation, processing or embedding reagent, or
    c) both a) and b).

4. The method of claim 3, wherein Argon is added to all liquid reagents that are contacted with the biological tissue specimen.

5. The method of claim 2 wherein adding Argon comprises bubbling or sparging the tissue fixation, processing or embedding reagent with Argon gas for a time sufficient to saturate the reagent with dissolved Argon.

6. The method of claim 5 wherein the step of forming and maintaining an Argon enriched atmosphere is performed for all liquid reagents that are contacted with the biological tissue specimen.

7. The method of claim 6 wherein the step of forming and maintaining an Argon enriched atmosphere is performed is in accordance with claim 3) sub-element c).

8. The method of claim 1 wherein the biological tissue specimen is a human tissue derived from a biopsy, a tumor resection, or other medical procedures.

9. The method of claim 1, wherein the tissue fixation, processing and embedding reagents are Formalin-Fixation Paraffin Embedding (FFPE) reagents.

10. The method of claim 8, wherein the tissue fixation reagent is a phosphate buffered, 10% Formalin solution having a pH of 6.8 to 7.2 at 25° C.

11. The method of claim 1, wherein the Argon is comprised in a gaseous source composition that is a) a blend of at least Argon and Nitrogen and/or b) at an Argon concentration≥95% by volume.

12. A liquid composition comprising an Argon enriched tissue fixation reagent, an Argon enriched tissue processing reagent or an Argon enriched tissue embedding reagent.

13. The liquid composition of claim 12 wherein the reagent is a FFPE reagent.

14. The liquid composition of claim 12 wherein the liquid composition is a phosphate buffered, 10% Formalin solution having a pH of 6.8 to 7.2 at 25° C.

15. A process for manufacturing an Argon enriched tissue fixation reagent, an Argon enriched tissue processing reagent or an Argon enriched tissue embedding reagent comprising the step of adding Argon to the tissue fixation reagent, adding Argon to the tissue processing reagent or adding Argon to the tissue embedding reagent to thereby form an Argon enriched tissue fixation reagent, an Argon enriched tissue processing reagent or an Argon enriched tissue embedding reagent.

16. The process of claim 15 wherein the reagent is a FFPE reagent.

17. The process of claim 15 comprising a step of bubbling or sparging an Argon gas through the tissue fixation reagent, tissue processing reagent or tissue embedding reagent until Argon saturation occurs.

* * * * *